US012653509B2

(12) United States Patent
Adam et al.

(10) Patent No.: US 12,653,509 B2
(45) Date of Patent: Jun. 16, 2026

(54) METHOD TO INDUCE EXFOLIATION OF CELLS AND/OR TISSUE FRAGMENTS FOR ENHANCED CYTOPATHOLOGIC CELL COLLECTION

(71) Applicant: Adenocyte Ltd., Beit Shemesh (IL)

(72) Inventors: Dan Adam, Haifa (IL); Emmanuel Loeb, Tel-Aviv Yaffo (IL)

(73) Assignee: Adenocyte Ltd., Jerusalem (IL)

( * ) Notice: Subject to any disclaimer, the term of this patent is extended or adjusted under 35 U.S.C. 154(b) by 710 days.

(21) Appl. No.: 17/367,658

(22) Filed: Jul. 6, 2021

(65) Prior Publication Data

US 2021/0330298 A1 Oct. 28, 2021

Related U.S. Application Data

(63) Continuation of application No. 17/028,588, filed on Sep. 22, 2020, now abandoned, which is a continuation-in-part of application No. PCT/US2019/023864, filed on Mar. 25, 2019.

(60) Provisional application No. 62/793,061, filed on Jan. 16, 2019, provisional application No. 62/752,823, filed on Oct. 30, 2018, provisional application No. 62/647,133, filed on Mar. 23, 2018.

(51) Int. Cl.
*A61B 10/00* (2006.01)
*A61K 38/22* (2006.01)
*G01N 33/574* (2006.01)

(52) U.S. Cl.
CPC ...... *A61B 10/0045* (2013.01); *A61K 38/2235* (2013.01); *G01N 33/57438* (2013.01); *A61B 2010/0061* (2013.01)

(58) Field of Classification Search
CPC .................................................. A61B 10/0045
See application file for complete search history.

(56) References Cited

U.S. PATENT DOCUMENTS

| | | | |
|---|---|---|---|
| 6,054,314 A * | 4/2000 | Kim | C12Q 1/34 |
| | | | 435/7.1 |
| 2006/0094984 A1 | 5/2006 | Wood et al. | |
| 2009/0246798 A1 | 10/2009 | Sy et al. | |
| 2016/0303402 A1 | 10/2016 | Tyler | |
| 2017/0105673 A1 | 4/2017 | Mitragotri et al. | |
| 2017/0290572 A1 | 10/2017 | Nakata et al. | |
| 2021/0052873 A1 | 2/2021 | Geva et al. | |
| 2021/0100534 A1 | 4/2021 | Rutenberg et al. | |

(Continued)

FOREIGN PATENT DOCUMENTS

| | | |
|---|---|---|
| EP | 3768172 | 2/2024 |
| JP | 2010-504102 | 2/2010 |

(Continued)

OTHER PUBLICATIONS

Requisition Dated Feb. 27, 2024 From the Innovation, Science and Economic Development Canada, Canadian Intellectual Property Office Re. Application No. 3,094,954. (4 Pages).

(Continued)

*Primary Examiner* — Joseph M Santos Rodriguez

(57) ABSTRACT

Methods and techniques for obtaining enriched cell samples from an organ in a subject using an ultrasound contrast agent and insonating. Contiguous fragments of epithelia are obtained which are useful for subsequent histological analysis and for informing therapy and other medical considerations.

27 Claims, 1 Drawing Sheet

Specification includes a Sequence Listing.

(56) References Cited

U.S. PATENT DOCUMENTS

| | | | | |
|---|---|---|---|---|
| 2021/0213307 A1* | 7/2021 | Kost | .................... | A61N 7/022 |
| 2021/0378642 A1 | 12/2021 | Adam et al. | | |

FOREIGN PATENT DOCUMENTS

| | | | | |
|---|---|---|---|---|
| JP | 2014-210189 | 11/2014 | | |
| JP | 2015-517350 | 6/2015 | | |
| JP | 2016-528217 | 9/2016 | | |
| JP | 7500536 | 6/2024 | | |
| WO | WO-9640285 A1 * | 12/1996 | ......... | A61K 49/0002 |
| WO | WO 2008/036765 | 3/2008 | | |
| WO | WO 2010/009141 | 1/2010 | | |
| WO | WO 2010/093861 | 8/2010 | | |
| WO | WO 2010/103469 | 9/2010 | | |
| WO | WO 2013/028548 | 2/2013 | | |
| WO | WO 2015/013448 | 1/2015 | | |
| WO | WO 2017/089800 | 6/2017 | | |
| WO | WO 2017/214050 | 12/2017 | | |
| WO | WO 2019/183623 | 9/2019 | | |

OTHER PUBLICATIONS

Supplementary European Search Report and the European Search Opinion Dated Dec. 1, 2021 From the European Patent Office Re. Application No. 19772197.0. (9 Pages).

International Preliminary Report on Patentability Dated Sep. 29, 2020 From the International Bureau of WIPO Re. Application No. PCT/US2019/023864. (9 Pages).

International Search Report and the Written Opinion Dated Sep. 5, 2019 From the International Searching Authority Re. Application No. PCT/US2019/023864. (14 Pages).

Hatfield et al. "Assessment of Endoscopic Retrograde Cholangio-Pancreatography (ERCP) and Pure Pancreatic Juice Cytology in Patients with Pancreatic Disease", Gut, 17(1): 14-21, Jan. 1976.

Restriction Official Action Dated Sep. 28, 2023 from the US Patent and Trademark Office Re. U.S. Appl. No. 17/028,588. (7 pages).

Notification of Office Action Dated Jan. 15, 2024 From the State Intellectual Property Office of the People's Republic of China Re. Application No. 201980033976.X. (4 Pages).

Translation Dated Jan. 31, 2024 of Notification of Office Action Dated Jan. 15, 2024 From the State Intellectual Property Office of the People's Republic of China Re. Application No. 201980033976. X. (6 Pages).

Notice of Reason(s) for Rejection Dated Feb. 28, 2023 From the Japan Patent Office Re. Application No. 2021-500509 and Its Translation Into English. (14 pages).

Translation Dated Apr. 5, 2024 of Grounds of Reason of Rejection Dated Mar. 25, 2024 From the Korean Intellectual Property Office Re. Application No. 10-2020-7030351 (4 Pages).

Notice of Reasons for Rejection Dated Nov. 24, 2023 From the Japan Patent Office Re. Application No. 2021-500509 and Its Translation Into English. (7 Pages).

Grounds of Reason of Rejection Dated Mar. 25, 2024 From the Korean Intellectual Property Office Re. Application No. 10-2020-7030351 (6 Pages).

Translation Dated Oct. 10, 2024 of Notification of Office Action and Search Report Dated Aug. 28, 2024 From the State Intellectual Property Office of the People's Republic of China Re. Application No. 201980033976.X. (9 Pages).

Restriction Official Action Dated Feb. 6, 2025 from the US Patent and Trademark Office Re. U.S. Appl. No. 17/404,797. (6 pages).

European Search Report and the European Search Opinion Dated Aug. 23, 2024 From the European Patent Office Re. Application No. 24159974.5. (10 Pages).

Final Notice of Rejection Dated Jan. 20, 2025 From the Korean Intellectual Property Office Re. Application No. 10-2020-7030351. together with Its English Translation (11 Pages).

Notification of Office Action and Search Report Dated Aug. 28, 2024 From the State Intellectual Property Office of the People's Republic of China Re. Application No. 201980033976.X and Its Machine Translation into English. (10 Pages).

Notice of Reason(s) for Rejection Dated Jun. 3, 2025 From the Japan Patent Office Re. Application No. 2024-091115 and Its Translation Into English. (12 Pages).

Grounds of Reason of Rejection Dated Oct. 30, 2025 From the Korean Intellectual Property Office Re. Application No. 10-2020-7030351 and its Machine Translation into English. (6 Pages).

Official Action Dated Aug. 21, 2025 from the US Patent and Trademark Office Re. U.S. Appl. No. 17/404,797. (45 pages).

Requisition Dated Sep. 11, 2025 From the Innovation, Science and Economic Development Canada, Canadian Intellectual Property Office Re. Application No. 3,094,954. (5 Pages).

Iwata et al. "Evaluation of Diagnostic Cytology via Endoscopic Naso-Pancreatic Drainage for Pancreatic Tumor", World Journal of Gastrointestinal Endoscopy, 6(8): 366-372, Aug. 16, 2014.

Communication Pursuant to Article 94(3) EPC Dated Mar. 24, 2026 From the European Patent Office Re. Application No. 24159974.5 (8 Pages).

Notice of Reason(s) for Rejection Dated Feb. 3, 2026 From the Japan Patent Office Re. Application No. 2024-091115 and Its Translation Into English. (7 Pages).

* cited by examiner

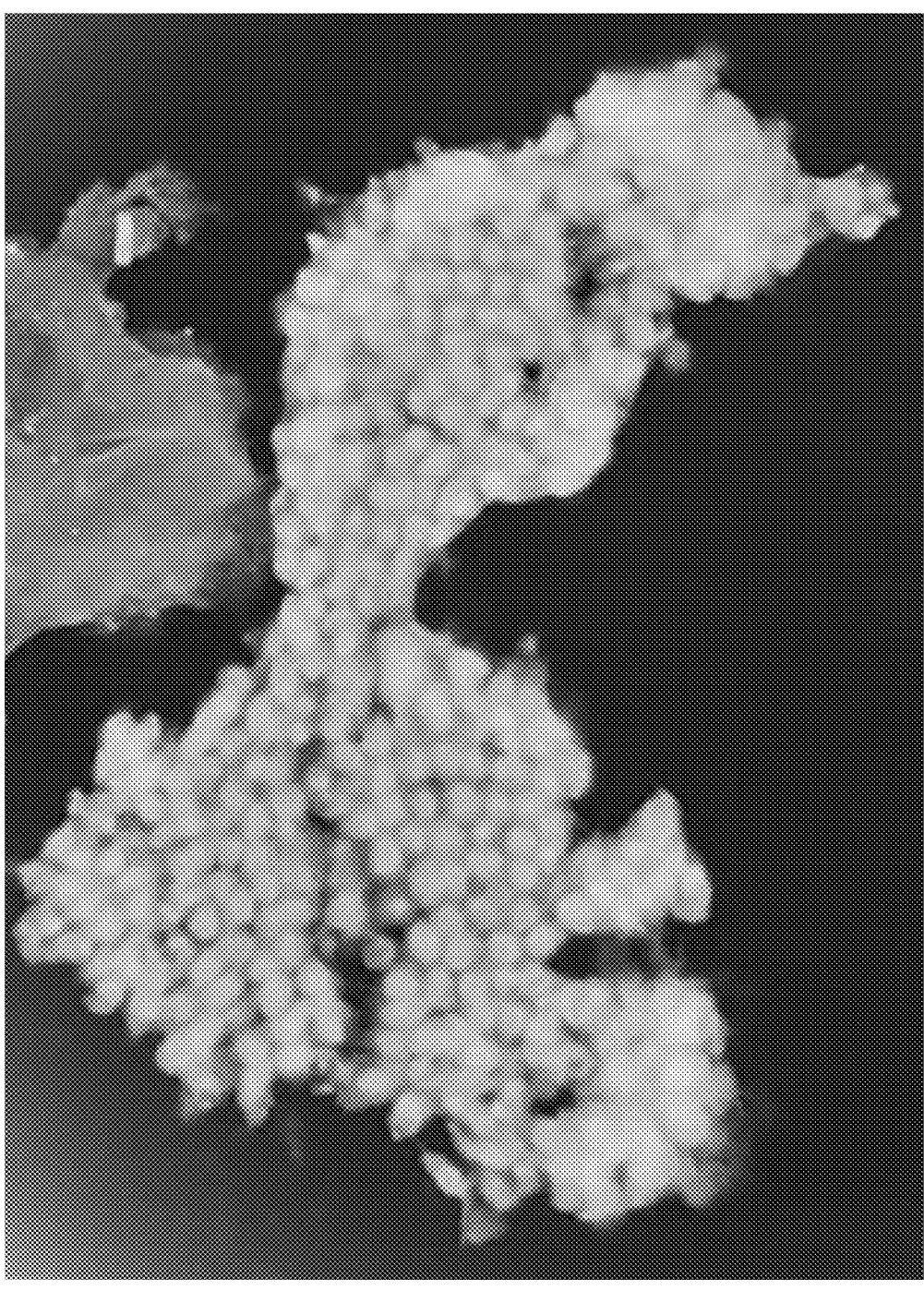

SEQUENCE LISTING

```
<160> NUMBER OF SEQ ID NOS: 1

<210> SEQ ID NO 1
<211> LENGTH: 27
<212> TYPE: PRT
<213> ORGANISM: HOMO SAPIENS

<400> SEQUENCE: 1

His Ser Asp Gly Thr Phe Thr Ser Glu Leu Ser Arg Leu Arg Asp Ser
1               5                   10                  15

Ala Arg Leu Gln Arg Leu Leu Gln Gly Leu Val
            20                  25
```

METHOD TO INDUCE EXFOLIATION OF CELLS AND/OR TISSUE FRAGMENTS FOR ENHANCED CYTOPATHOLOGIC CELL COLLECTION

RELATED APPLICATIONS

This application is a continuation of U.S. patent application Ser. No. 17/028,588 filed on Sep. 22, 2020, which is a Continuation-in-Part (CIP) of PCT Patent Application No. PCT/US2019/023864 having International Filing Date of Mar. 25, 2019, which claims the benefit of priority of U.S. Provisional Application Nos. 62/647,133 filed on Mar. 23, 2018, 62/752,823 filed on Oct. 30, 2018 and 62/793,061 filed on Jan. 16, 2019.

The contents of the above applications are all incorporated by reference as if fully set forth herein in their entirety.

SEQUENCE LISTING STATEMENT

The ASCII file, entitled 88673SequenceListing.txt, created on Jul. 6, 2021, comprising 694 bytes, submitted concurrently with the filing of this application is incorporated herein by reference.

FIELD AND BACKGROUND OF THE INVENTION

Over 95% of cancers in adults are carcinomas, meaning that they originate in the epithelial lining of an organ. In many cases these epithelia are in direct contact with a surrounding body fluid into which the epithelial cells are continually shed as part of the natural process of epithelial regeneration. An example are pancreatic ductal cells that are continually being shed into the pancreatic juice, lung cells that are continually shed into the sputum, and bladder cells that are continually being shed into the urine. Dysplastic and cancer cells that may be present in the subject epithelium are also naturally shed into the surrounding fluid along with normal epithelial cells. In many cases these body fluids are accessible to non-invasive or minimally invasive sampling methods. Exfoliated cells found in these sampled fluids can then be concentrated using standard laboratory techniques for subsequent microscopic evaluation by a cytopathologist allowing in theory for the early detection of dysplasia and cancer. While cytopathologic examination of cells exfoliated into surrounding body fluids generally has high specificity, its sensitivity for the detection of dysplasia and cancer is often limited by the fact that the slow rate of natural exfoliation of epithelial cells into the surrounding fluid results in a very small sample with few cells for the pathologist to examine. This currently limits the cytopathologic detection of dysplasia and cancer in: the mediastinum, the pleura, the pericardium, the peritoneum, the lung, the breast, the salivary glands, the meninges, the pancreatic ducts, pancreatic cysts, the kidney, the liver, the bladder, and the ovaries among others.

For example, the pancreas is comprised of a variety of cell types, each of which may give rise to a different type of cancer. Pancreatic ductal adenocarcinoma (PDAC) is the fourth leading cause of cancer-related death in the United States. This is due to its often late diagnosis at metastatic stages, its aggressive biology, and only partial response to known chemotherapies. Cytological evaluation of pancreatic juice has been shown to have a high-sensitivity, upwards of 79% in diagnosing pancreatic cancer.

Because there are usually few or no early symptoms, pancreatic cancer is often advanced by the time it is discovered. For this reason, by 2030, pancreatic cancer is projected to be the second leading cause of cancer death in the United States (1).

Pancreatic screening and surveillance is performed for patients at increased risk for developing pancreatic cancer because of their pancreatic cancer family history, a pancreatic cancer susceptibility gene mutation, or having incidentally detected pancreatic cysts.

Current tests for pancreatic cancer include endoscopic ultrasonography (EUS) and endoscopic magnetic resonance imaging/magnetic resonance cholangiopancreatography (ERCP). Although these tests are accurate for detecting pancreatic cysts (2, 3, 4) they are not well suited for detecting small solid pancreatic cancers, as evidenced by the number of patients who develop pancreatic cancer despite regular surveillance. This reflects missed opportunities for early detection (5).

Cytopathology, an essential clinical criterion in the diagnosis of disease, has been tested as a diagnostic modality for pancreatic cancer. For example, in 1974, Yoshihiko Endo and coworkers first reported the cytodiagnosis of pancreatic cancer from the collection of pancreatic juice with a duodenoscope (6). They reported a sensitivity of 79%. Through the subsequent decades, many researchers have attempted to use cytologic examination of pancreatic juice to determine pancreatic malignancy, but sensitivity ranges remained stubbornly around 70-80% (7, 8). The shortfall in sensitivity observed from multiple endoscopists through multiple years, likely reflect shortcomings in typical cell collection and analysis methods. In addition, low levels of cells or tissue fragments in fluid samples obtained for histological analysis in bioassays is a problem that exists for multiple bioassay types.

Thus, there is a need for increasing the yield of cells exfoliated from various organs and tissue types for collection and subsequent analysis in order to enhance the specificity of such diagnostic tests. There also is a need to induce the exfoliation of intact tissue, which may be used to provide an enface view of a tissue segment. In regard to pancreatic cancer in particular, there is a need for improved cellular collection and tissue fragment collection techniques for detecting rare cells from a background of normal cells in the pancreas.

SUMMARY OF THE INVENTION

Embodiments of the invention set forth herein provide methods and systems for obtaining cells, and/or tissue fragments and other molecules at a much greater rate than previously observed by different means. In an embodiment the method includes administering an ultrasound contrast agent that forms microbubbles in a patient's circulatory system and insonating the subject. After introducing microbubbles the organ or tissue, such as a pancreas, is subjected to wide area ultrasound energy. The ultrasound application of embodiments of the invention may be described as Low Intensity Non-Focused Ultrasound (LINFU). In embodiments of the invention, the ultrasound energy combined with the energy exerted by the microbubbles causes pancreatic cells and, optionally, tissue fragments to disassociate and/or exfoliate. The patient, in the case of obtaining a pancreas sample, is subsequently injected with secretin, a drug that induces pancreatic secretion. In this regard, some of the exfoliated and dislodged cells and tissue fragments may be deposited into the pancreatic juice, which is then collected endoscopically. The cells and/or tissue fragments in the enriched samples obtained are then analyzed morphologically and/or using molecular biomarkers to detect a presence or absence of cellular abnormality.

These procedures can dramatically increase the total number of cells to be expressed in the pancreatic juice. Moreover, the procedures set forth herein may induce the separation of intact tissue fragments from the pancreas.

These procedures, when applied to the other organs or body sites, such as, the mediastinum, pleura, pericardium, peritoneum, lung, breast, salivary glands, meninges, pancreatic ducts, pancreatic cysts, kidney, liver, bladder, or ovaries, may dramatically increase the total number of cells to be expressed in the surrounding fluids of such organs. Additionally, the procedures set forth herein may additionally induce the separation of intact tissue fragments from the above-cited exemplary organs. For example, the procedures set forth herein are utilized to induce exfoliation of lung cells into surrounding sputum or to induce to the exfoliation of bladder cells and bladder tissue into surrounding urine.

A method is provided of obtaining a cell sample from an organ a subject comprising: administering an amount of an ultrasound contrast agent to the subject; and insonating the organ of the subject with an amount of ultrasonic energy effective to elicit stable cavitation of the ultrasound contrast agent, so as to thereby elicit exfoliation of cells or an epithelia tissue fragment from the organ in a subject.

Also provided is a method of obtaining pancreatic cells from a subject comprising: administering an amount of an ultrasound contrast agent to the subject; and insonating a pancreas of the subject to an amount of ultrasonic energy effective to elicit stable cavitation of an ultrasound contrast agent, so as to thereby elicit exfoliation of cells into a duct of a pancreas in a subject.

Also provided is a method of obtaining pancreatic cells from a subject comprising: insonating a pancreas of the subject with an amount of single frequency ultrasonic energy effective to elicit exfoliation of cells into a duct of a pancreas in a subject.

Also provided is a method of obtaining pancreatic cells from a subject comprising: insonating a pancreas of the subject with an amount of ultrasonic energy from a multi-frequency array effective to achieve an asymmetric ultrasound wave at a predetermined point in the pancreas and elicit exfoliation of cells into a duct of a pancreas in the subject.

Also provided is a method of treating a subject for a pancreatic disorder comprising:

a) determining if the subject has pancreatic dysplastic cells or pancreatic cancer cells in their pancreas by the method described herein, and b) effecting chemotherapy, radiotherapy, immunotherapy or a pancreatectomy in a subject found in a) to have pancreatic dysplastic cells or pancreatic cancer cells in their pancreas.

In embodiments, the determining if the subject has pancreatic dysplastic cells or pancreatic cancer cells in their pancreas is effected through one or more of cellular morphological analysis, tissue morphological analysis, or biomolecular marker analysis.

Also provided is a method of increasing the efficacy of cell sample collection from a tissue in an assay procedure on a subject comprising, prior to collecting a cell sample from the tissue, insonating the tissue of the subject with an amount of ultrasonic energy effective to elicit stable cavitation of the ultrasound contrast agent so as to thereby elicit exfoliation of cells or tissue fragments from the in a subject and then collecting a cell sample from the tissue in the subject Also provided is a method of performing an assay on a sample of cells or tissue from a subject so as to determine if the cells or tissue comprise cancerous or precancerous cells or tissue, comprising:

a) receiving a sample of cells or tissue, wherein the sample has been previously obtained by a method of administering an amount of an ultrasound contrast agent to the subject; and insonating the organ of the subject with an amount of ultrasonic energy effective to elicit stable cavitation of the ultrasound contrast agent, so as to thereby elicit exfoliation of cells or an epithelia tissue fragment from the organ in a subject, and collecting a sample of the exfoliated cells or tissue;

b) performing one of cellular morphological analysis, tissue morphological analysis, or biomolecular marker analysis, so as to determine if the cells or tissue comprise cancerous or precancerous cells or tissue.

Also provided is a method for the early detection of dysplastic and cancerous cells in the pancreas comprising of the application of ultrasound energy directed to the pancreas to induce cellular exfoliation, followed by endoscopic collection of the pancreatic fluid containing the exfoliated cells and cell clusters for molecular examination and microscopic morphological examination.

Also provided is an isolated sample of a body fluid, wherein the sample has been directly obtained from a subject who has had a tissue or organ insonated, wherein the sample comprises epithelial or other cells from the tissue or organ at a level more than 2× enriched compared to the level of epithelial or other cells in an otherwise identical sample obtained from a subject who has not been insonated.

Also provided is a method of obtaining a sample of contiguous pancreatic duct cells from a subject comprising:

administering to the subject, within one hour before or after initiation of insonation with ultrasonic energy, an amount of a secretin polypeptide effective to elicit pancreatic secretion; insonating a pancreas of the subject with an amount of ultrasonic energy at a predetermined point in the pancreas and elicit exfoliation of cells into a duct of a pancreas in the subject; and then removing a sample of fluid containing contiguous pancreatic duct cells from the subject.

BRIEF DESCRIPTION OF THE SEVERAL VIEWS OF THE DRAWING

FIG. 1: A large fragment of pancreatic epithelial tissue obtained from pancreatic fluid collected subsequent to insonating an animal as described in Example 1 hereinbelow.

DESCRIPTION OF SPECIFIC EMBODIMENTS OF THE INVENTION

A method is provided of obtaining a cell sample from an organ a subject comprising: administering an amount of an ultrasound contrast agent to the subject; and insonating the organ of the subject with an amount of ultrasonic energy effective to elicit stable cavitation of the ultrasound contrast agent, so as to thereby elicit exfoliation of cells or an epithelia tissue fragment from the organ in a subject.

In embodiments, the cells comprise epithelial cells.

In embodiments, an epithelia tissue fragment of an epithelia of the organ is exfoliated.

In embodiments, the organ is a bladder, breast, liver, kidney, lung thyroid, gastrointestinal tract or pancreas. The organ from which the cell sample is to be collected can be known as the target organ.

In embodiments, the insonation is applied so as to not insonate any other organ other than the target organ. In embodiments, the insonation is applied so as to not elicit stable cavitation in any organ other than the target organ. In embodiments, the ultrasound contrast agent is applied so as to selectively accumulate in the target organ. In embodiments, the insonation and/or the ultrasound contrast agent are temporally applied so as to selectively elicit stable cavitation in no organ other than the target organ. In embodiments, the insonation and/or the ultrasound contrast agent are spatially applied so as to selectively elicit stable cavitation in no organ other than the target organ. In embodiments, the insonation and/or the ultrasound contrast agent are temporally and spatially applied so as to selectively elicit stable cavitation in no organ other than the target organ. In embodiments, the insonation is temporally applied so as to selectively insonate only the target organ. In embodiments, the insonation is spatially applied so as to selectively insonate only the target organ. In embodiments, the insonation is temporally and spatially applied so as to selectively insonate only the target organ.

In embodiments, the method further comprises removing a sample of fluid containing the cells from the subject.

In embodiments, the sample of fluid is obtained from a cyst of the organ.

In embodiments, the sample of fluid is obtained from a secretion of the organ.

Also provided is a method of obtaining pancreatic cells from a subject comprising: administering an amount of an ultrasound contrast agent to the subject; and insonating a pancreas of the subject to an amount of ultrasonic energy effective to elicit stable cavitation of an ultrasound contrast agent, so as to thereby elicit exfoliation of cells into a duct of a pancreas in a subject.

In embodiments, the ultrasonic energy does not exceed a Mechanical Index of 0.03, or does not exceed a Mechanical Index of 0.05.

A method of obtaining a sample of contiguous pancreatic duct cells from a subject comprising: administering an amount of an ultrasound contrast agent to the subject, and administering to the subject within one hour before or after initiation of insonation with ultrasonic energy, an amount of a secretin polypeptide effective to elicit pancreatic secretion; insonating a pancreas of the subject with an amount of ultrasonic energy at a Mechanical Index of from 0.03 to 1.3 from a multi-frequency array effective to achieve an asymmetric ultrasound wave at a predetermined point in the pancreas and elicit exfoliation of cells into a duct of a pancreas in the subject; and then removing a sample of fluid containing contiguous pancreatic duct cells from the subject.

Also provided is a method of obtaining pancreatic cells from a subject comprising: insonating a pancreas of the subject with an amount of single frequency ultrasonic energy effective to elicit exfoliation of cells into a duct of a pancreas in a subject.

In embodiments, the ultrasonic energy is at a Mechanical Index of from 0.03 to 1.3.

Also provided is a method of obtaining pancreatic cells from a subject comprising: insonating a pancreas of the subject with an amount of ultrasonic energy from a multi-frequency array effective to achieve an asymmetric ultrasound wave at a predetermined point in the pancreas and elicit exfoliation of cells into a duct of a pancreas in the subject.

In embodiments, the ultrasonic energy is at a Mechanical Index of from 0.03 to 1.3.

Also provided is a method of obtaining a sample of contiguous pancreatic duct cells from a subject comprising:

administering to the subject, within one hour before or after initiation of insonation with ultrasonic energy, an amount of a secretin polypeptide effective to elicit pancreatic secretion; insonating a pancreas of the subject with an amount of ultrasonic energy at a predetermined point in the pancreas and elicit exfoliation of cells into a duct of a pancreas in the subject; and then removing a sample of fluid containing contiguous pancreatic duct cells from the subject. Contiguous cells are two or more cells wherein each of the cells is attached to at least one other cell. For example a fragment of epithelia tissue, or a sheet of cells.

In embodiments, the ultrasonic energy is at a Mechanical Index of from 0.03 to 1.3.

In embodiments, the methods further comprise administering to the subject, within one hour before or after initiation of insonation with the ultrasonic energy, an amount of a secretin polypeptide, or other substance that elicits pancreatic secretion, effective to elicit pancreatic secretion.

In embodiments, the method comprises administering the amount of secretin, or other substance that elicits pancreatic secretion, with the amount of an ultrasound contrast agent.

In embodiments, the secretin is administered and is a human secretin.

In embodiments, the methods further comprise positioning a catheter or other collecting device at an opening of a pancreatic duct in the subject.

In embodiments, the opening of a pancreatic duct is a duodenal papilla.

In embodiments, the methods further comprise obtaining a sample of pancreatic secretion using the catheter or other collecting device.

In embodiments, the methods further comprise analyzing the sample of the pancreatic secretion obtained so as to determine if the sample contains pancreatic cancer cells or pancreatic dysplasia cells, or is non-pathological.

In embodiments, computer-assisted analysis is used in identifying the cells as cancerous or dysplastic. In embodiments, cellular morphological, tissue morphological and/or molecular biological analysis is used in identifying the cells as cancerous or dysplastic.

In embodiments, the method is effective to elicit exfoliation of ductal and/or acinar cells of the pancreas.

In embodiments, the method is effective to elicit exfoliation of an epithelial tissue fragment of the pancreas.

In embodiments, the amount of ultrasonic energy elicits stable cavitation in the pancreas of the subject.

In embodiments, the amount of ultrasonic energy does not elicit inertial cavitation or implosion of microbubbles within the organ of the subject.

In embodiments, the amount of ultrasonic energy does not elicit inertial cavitation or implosion of microbubbles within the pancreas of the subject.

In embodiments, the methods further comprise monitoring the subject for implosion of microbubbles or ultrasound contrast agent during at least a portion of the insonating of the subject.

In embodiments, the amount of ultrasonic energy is effective to generate a plurality of microbubbles in an organ of a subject.

In embodiments, the ultrasonic energy is unfocused in the organ of the subject.

In embodiments, the ultrasonic energy is unfocused in the pancreas of a subject.

In embodiments, the ultrasonic energy is partially unfocused.

In embodiments, the ultrasonic energy is focused in the organ of the subject.

In embodiments, the ultrasonic energy is focused in the pancreas of a subject.

In embodiments, the ultrasound contrast agent comprises microspheres.

In embodiments, the contrast agent is not be applied directly to the pancreas, but is administered intravenously.

In embodiments, the ultrasound contrast agent comprises sulfur hexafluoride lipid-type A microspheres.

In embodiments, the ultrasound energy is emitted from a transducer touching the skin of the subject or adjacent thereto, and wherein the closest point of the transducer is within 2 to 4 inches of a surface of the pancreas of the subject.

In embodiments, the Mechanical Index does not exceed 0.03.

In embodiments, the Mechanical Index does not exceed 0.05.

In embodiments, the frequency of the insonated ultrasound energy comprises 1.5 MHz to 3.0 MHz.

In embodiments, the ultrasound energy is emitted from a transducer touching the skin of the subject or adjacent thereto, and wherein the closest point of the transducer is at a position greater than 4 and up to 9 inches from a surface of the pancreas of the subject.

In embodiments, the Mechanical Index does not exceed 0.03.

In embodiments, the Mechanical Index does not exceed 0.05.

In embodiments, the frequency of the insonated ultrasound energy comprises 1.0 MHz to 1.5 MHz.

In embodiments, the ultrasound energy is emitted from a transducer array which is from 3 to 5 inches long by 1 to 3 inches wide.

In embodiments, the ultrasound energy is emitted from an imaging probe and an ultrasound imaging system.

In embodiments, the ultrasound energy is emitted from a volumetric probe and an ultrasound imaging system.

In embodiments, the ultrasound energy is emitted from a transducer array which is substantially triangular in shape.

In embodiments, the ultrasound energy is emitted from a transducer array which is substantially rectangular in shape.

In embodiments, the ultrasound energy is emitted from a flexible transducer array.

In embodiments, the ultrasound energy is emitted from an transducer array that includes several cavitation detectors for monitoring and localizing cavitation during the procedure.

In embodiments, the ultrasound is emitted from a transducer array which is attached by a belt to the subject.

In embodiments, the subject is insonated with the amount of ultrasonic energy for greater than 5 minutes.

In embodiments, the subject is insonated with the amount of ultrasonic energy for less than 15 minutes.

In embodiments, the subject is administered the amount of an ultrasound contrast agent within 1 hour before initiation of the subject being insonated with the amount of ultrasonic energy.

In embodiments, the subject is administered the amount of an ultrasound contrast agent within 30 minutes before initiation of the subject being insonated with the amount of ultrasonic energy.

In embodiments, the subject is administered the amount of secretin within 1 hour of initiation of the subject being insonated with the amount of ultrasonic energy.

In embodiments, the subject is administered the amount of secretin within 30 minutes of initiation of the subject being insonated with the amount of ultrasonic energy.

In embodiments, the subject is administered the amount of secretin before initiation of being insonated with the amount of ultrasonic energy.

In embodiments, the subject is administered the amount of secretin after initiation of being insonated with the amount of ultrasonic energy.

In embodiments, the subject is administered the amount of secretin less than 10 minutes after termination of being insonated with the amount of ultrasonic energy.

In embodiments, the subject is administered the amount of secretin during insonation with the amount of ultrasonic energy.

In embodiments, the subject is administered the amount of secretin and ultrasound contrast agent simultaneously.

In embodiments, the ultrasound imaging is used to assist placement of a transducer which emits the ultrasonic energy over the organ or over the pancreas.

In embodiments, the ultrasound imaging is used to assist placement of a catheter or other collecting device at an opening of a pancreatic duct in the subject.

In embodiments, the ultrasound imaging is used to assist placement of a catheter or other fluid collecting device in or adjacent to the organ in the subject.

In embodiments, the subject is not administered an ultrasound contrast agent.

In embodiments, the ultrasound contrast agent is administered intravenously.

In embodiments, the ultrasound contrast agent is only administered intravenously.

In embodiments, the ultrasonic energy is multi-frequency and/or multi-phase.

In embodiments, the subject is insonated dynamically with ultrasonic energy.

In embodiments, the amount of ultrasonic energy is insonated from more than one position on a first lateral plane.

In embodiments, the amount of ultrasonic energy is insonated from more than one position on a second lateral plane perpendicular to the first lateral plane.

In embodiments, the pancreas of the subject is exposed to an amount of ultrasonic irradiation in at least two different positions on a coronal, sagittal or transverse plane of the pancreas.

In embodiments, the organ of the subject is exposed to an amount of ultrasonic irradiation in at least two different positions on a coronal, sagittal or transverse plane of the organ.

In embodiments, the subject is supine. In embodiments, the subject is sitting. In embodiments, the subject is standing.

In embodiments, the subject is human.

Also provided is a method of treating a subject for a pancreatic disorder comprising:

a) determining if the subject has pancreatic dysplastic cells or pancreatic cancer cells in their pancreas by the method described herein, and b) effecting chemotherapy, radiotherapy, immunotherapy or a pancreatectomy in a subject found in a) to have pancreatic dysplastic cells or pancreatic cancer cells in their pancreas.

In embodiments, the determining if the subject has pancreatic dysplastic cells or pancreatic cancer cells in their pancreas is effected through one or more of cellular morphological analysis, tissue morphological analysis, or biomolecular marker analysis.

Also provided is a method of increasing the efficacy of cell sample collection from a tissue in an assay procedure on a subject comprising, prior to collecting a cell sample from the tissue, insonating the tissue of the subject with an amount of ultrasonic energy effective to elicit stable cavitation of the ultrasound contrast agent so as to thereby elicit exfoliation of cells or tissue fragments from the in a subject and then collecting a cell sample from the tissue in the subject In embodiments, the tissue comprises epithelial cells.

Also provided is a method of performing an assay on a sample of cells or tissue from a subject so as to determine if the cells or tissue comprise cancerous or precancerous cells or tissue, comprising:

a) receiving a sample of cells or tissue, wherein the sample has been previously obtained by a method of administering an amount of an ultrasound contrast agent to the subject; and insonating the organ of the subject with an amount of ultrasonic energy effective to elicit stable cavitation of the ultrasound contrast agent, so as to thereby elicit exfoliation of cells or an epithelia tissue fragment from the organ in a subject, and collecting a sample of the exfoliated cells or tissue;

b) performing one of cellular morphological analysis, tissue morphological analysis, or biomolecular marker analysis, so as to determine if the cells or tissue comprise cancerous or precancerous cells or tissue.

In embodiments, the methods further comprise administering the amount of an ultrasound contrast agent to the subject and insonating the organ of the subject with an amount of ultrasonic energy effective to elicit stable cavitation of the ultrasound contrast agent so as to thereby elicit exfoliation of cells or an epithelia tissue fragment from the organ in a subject and collecting a sample of the exfoliated cells or tissue.

Also provided is a method for the early detection of dysplastic and cancerous cells in the pancreas comprising of the application of ultrasound energy directed to the pancreas to induce cellular exfoliation, followed by endoscopic collection of the pancreatic fluid containing the exfoliated cells and cell clusters for molecular examination and microscopic morphological examination.

In embodiments, the ultrasound energy directed to the pancreas to increase cellular exfoliation into pancreatic juice is applied external to a patient's body.

In embodiments, the ultrasound energy directed to the pancreas to increase cellular exfoliation into pancreatic juice is applied endoscopically.

In embodiments, the administration of ultrasound energy to increase exfoliation is combined with the administration of secretin, a hormone that increases the production of pancreatic fluid.

In embodiments, the pancreatic juice is examined with the aid of neural network based computer-assisted microscopy system.

Also provided is an isolated sample of a body fluid, wherein the sample has been directly obtained from a subject who has had a tissue or organ insonated, wherein the sample comprises epithelial or other cells from the tissue or organ at a level more than 2× enriched compared to the level of epithelial or other cells in an otherwise identical sample obtained from a subject who has not been insonated.

In embodiments, the subject was also administered an ultrasound contrast agent present during the insonation of the tissue or organ.

In embodiments, the pancreas of the subject has been insonated and secretin has been administered to the subject prior to the sample having been directly obtained from the subject.

In embodiments, the organ is a bladder, breast, liver, kidney, lung, thyroid, gastrointestinal tract or cist. In order to increase the yield of cells of interest, e.g. abnormal cells in a fluid sample from the body, the subject invention utilizes an application of ultrasound energy, preferably at a level that is safe for diagnostic purposes (e.g. Mechanical Index ("MI") of 1.9 or lower).

In embodiments, the subject is insonated with ultrasound energy at an MI of 0.01. In embodiments, the subject is insonated with ultrasound energy at an MI of 0.02. In embodiments, the subject is insonated with ultrasound energy at an MI of 0.03. In embodiments, the subject is insonated with ultrasound energy at an MI of 0.04. In embodiments, the subject is insonated with ultrasound energy at an MI of 0.05. In embodiments, the subject is insonated with ultrasound energy at an MI of 0.06. In embodiments, the subject is insonated with ultrasound energy at an MI of 0.07. In embodiments, the subject is insonated with ultrasound energy at an MI of 0.08. In embodiments, the subject is insonated with ultrasound energy at an MI of 0.09. In embodiments, the subject is insonated with ultrasound energy at an MI of 0.1. In embodiments, the subject is insonated with ultrasound energy at an MI of 0.11. In embodiments, the subject is insonated with ultrasound energy at an MI of 0.12. In embodiments, the subject is insonated with ultrasound energy at an MI of 0.13. In embodiments, the subject is insonated with ultrasound energy at an MI of 0.14. In embodiments, the subject is insonated with ultrasound energy at an MI of 0.15. In embodiments, the subject is insonated with ultrasound energy at an MI of 0.16. In embodiments, the subject is insonated with ultrasound energy at an MI of 0.17. In embodiments, the subject is insonated with ultrasound energy at an MI of 0.18. In embodiments, the subject is insonated with ultrasound energy at an MI of 0.19. In embodiments, the subject is insonated with ultrasound energy at an MI of 0.2. In embodiments, the subject is insonated with ultrasound energy at an MI of 0.3. In embodiments, the subject is insonated with ultrasound energy at an MI of 0.4. In embodiments, the subject is insonated with ultrasound energy at an MI of 0.5. In embodiments, the subject is insonated with ultrasound energy at an MI of 0.6. In embodiments, the subject is insonated with ultrasound energy at an MI of 0.7. In embodiments, the subject is insonated with ultrasound energy at an MI of 0.8. In embodiments, the subject is insonated with ultrasound energy at an MI of 0.9. In embodiments, the subject is insonated with ultrasound energy at an MI of 1.0. In embodiments, the subject is insonated with ultrasound energy at an MI of 1.1. In embodiments, the subject is insonated with ultrasound energy at an MI of 1.2. In embodiments, the subject is insonated with ultrasound energy at an MI of 1.3. In embodiments, the subject is insonated with ultrasound energy at an MI of 1.4. In embodiments, the subject is insonated with ultrasound energy at an MI of 1.5. In embodiments, the subject is insonated with ultrasound energy at an MI of 1.6.

In embodiments, the subject is insonated with ultrasound energy at an MI of 1.7. In embodiments, the subject is insonated with ultrasound energy at an MI of 1.8. In embodiments, the subject is insonated with ultrasound energy at an MI of 1.9. In embodiments, the subject is insonated with ultrasound energy at an MI of 2.0.

The patient is subjected to ultrasound energy for a period of time prior to cell collection. In embodiments, the subject is insonated with ultrasound energy for 1 minute. In embodiments, the subject is insonated with ultrasound energy for 2 minutes. In embodiments, the subject is insonated with ultrasound energy for 3 minutes. In embodiments, the subject is insonated with ultrasound energy for 4 minutes. In embodiments, the subject is insonated with ultrasound energy for 5 minutes. In embodiments, the subject is insonated with ultrasound energy for 6 minutes. In embodiments, the subject is insonated with ultrasound energy for 7 minutes. In embodiments, the subject is insonated with ultrasound energy for 8 minutes. In embodiments, the subject is insonated with ultrasound energy for 9 minutes. In embodiments, the subject is insonated with ultrasound energy for 10 minutes. In embodiments, the subject is insonated with ultrasound energy for 10-15 minutes. In embodiments, the subject is insonated with ultrasound energy for 15-20 minutes.

In embodiments the frequency of the insonated ultrasound energy comprises 1.0 MHz to 1.5 MHz. In embodiments the frequency of the insonated ultrasound energy comprises 1.0 MHz to 3.0 MHz. In embodiments the frequency of the insonated ultrasound energy comprises 1.5 MHz to 3.0 MHz. In embodiments the frequency of the insonated ultrasound energy comprises 1.5 MHz to 2.0 MHz. In embodiments the frequency of the insonated ultrasound energy comprises 2.0 MHz to 3.5 MHz. In embodiments the frequency of the insonated ultrasound energy comprises 2.5 MHz to 3.0 MHz. In embodiments the frequency of the insonated ultrasound energy comprises less than 1.0 MHz.

In embodiments, the subject is insonated with ultrasound energy with a pulse length of 1 microsecond to 400 microseconds. In embodiments, the subject is insonated with ultrasound energy with a pulse length of 20 microseconds to 400 microseconds. In embodiments, the subject is insonated with ultrasound energy with a pulse length of 400 microseconds. In embodiments, the subject is insonated with ultrasound energy with a pulse length of 2 microseconds. In embodiments, the subject is insonated with ultrasound energy with a pulse length of 0.8 to 1.2 microseconds. In embodiments, the subject is insonated with ultrasound energy with a pulse length of 1.8 to 2.2 microseconds. In embodiments, the subject is insonated with ultrasound energy with a pulse length of 380 to 420 microseconds.

In embodiments the waveform of the insonated ultrasound energy comprises negative peaks of higher amplitude than positive peaks. In embodiments the waveform of the insonated ultrasound energy comprises negative peaks of lower amplitude than positive peaks. In embodiments the waveform of the insonated ultrasound energy comprises negative peaks of equal amplitude to the positive peaks. Such enhanced ultrasound may be achieved by means known in the art, for example, see U.S. Pat. No. 7,905,836, Dan Adam, issued Mar. 15, 2011, hereby incorporated by reference.

In embodiments the insonated ultrasound energy does not cause heating of the skin or does not cause heating of the tissues of the subject. In embodiments the insonated ultrasound energy is applied extracorporeally to the subject. In embodiments the insonated ultrasound energy is applied from within the subject, for example, via an endoscopic ultrasound transducer.

In embodiments of the invention, insonation of ultrasound energy is preceded by or is concurrently with an administration to the subject of a microbubble ultrasound contrast agent. In embodiments, the contrast agent is commercially available Lumason®. In embodiments, the ultrasound contrast agent comprises sulfur hexafluoride lipid-type A microspheres.

In embodiments of the invention, ultrasound energy combined with microbubbles circulating in the patient's circulatory system imparts sufficient energy to induce exfoliation of cells and, optionally, intact tissue fragments, from the organ, preferably an epithelia of the organ.

In embodiments regarding the pancreas, pancreatic juice is obtained during an upper endoscopy procedure. For example, after intravenous secretin administration, a disposable aspiration catheter is passed into the duodenum for collection of pancreas juice. Alternatively, pancreatic juice is collected by direct aspiration of duodenal fluid through the suction channel of the endoscope. After obtaining the pancreatic juice, the cellular content thereof can be, for example, affixed to one or more specimen slides. The specimen slides can then be processed and prepared for diagnostic analysis.

In embodiments regarding the pancreas, the secretin administered is human. In embodiments, the secretin administered is human, bovine or porcine. One useful form of human secretin is manufactured by ChiRhoClin, Inc. (Burtonsville, Md.) with the tradename "CHIRHOSTIM". Hum, an secretin in an embodiment has the sequence His-Ser-Asp-Gly-Thr-Phe-Thr-Ser-Glu-Leu-Ser-Arg-Leu-Arg-Asp-Ser-Ala-Arg-Leu-Gln-Arg-Leu-Leu-Gln-Gly-Leu-Val; SEQ ID NO: 1. One useful form of porcine secretin is manufactured by ChiRhoClin, Inc. (Burtonsville, Md.) and sold under the trade name "SECREFLO" by Repligen Corporation (Waltham, Mass.). Another useful form of porcine secretin is manufactured by ChiRhoClin, Inc. (Burtonsville, Md.) with the tradename "SECREMAX". A useful form of human secretin is manufactured and sold by ChiRhoClin, Inc. under the tradename "SECRETIN-HUMAN". The secretin may be combined in a composition with a pharmaceutically acceptable carrier and administered as such a composition. The secretin can be administered by any manner known in the art. In an embodiment, the secretin, or composition containing secretin, is administered intravenously. In an embodiment of any of the methods herein, secretin can be administered to the subject prior to or during the method.

"And/or" as used herein, for example, with option A and/or option B, encompasses the separate embodiments of (i) option A, (ii) option B, and (iii) option A plus option B. All combinations of the various elements described herein are within the scope of the invention unless otherwise indicated herein or otherwise clearly contradicted by context.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Where a numerical range is provided herein, it is understood that all numerical subsets of that range, and all the individual integers, and to the 2nd decimal place, contained therein, are provided as part of the invention. Thus, frequency of 1.5 to 2.0 MHz length includes the subset of frequencies 1.51 to 1.61 MHz, and the subset of frequencies 1.7 to 2.0 MHz, and the subset of frequencies 1.65 to 1.85 MHz, and so on and so forth, unless specially indicated otherwise.

While this invention has been described in conjunction with the embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

EXPERIMENTAL EXAMPLES

Example 1

A pig, denied food for 24 hours beforehand, was anesthetized for comfort and placed in a supine position on its side. Fluoroscopy was used to place a collecting catheter at an outlet of the pig's pancreas into the duodenum. The pig was intravenously administered an ultrasound contrast agent (Lumason® by Bracco Imaging; sulfur hexafluoride lipid-type A microspheres). Before the animal was insonated with ultrasound the area adjacent to the outlet of the pancreas (in the vicinity of the Ampulla of Vater/sphincter of Oddi) was cleaned using catheter suction. The animal was insonated with ultrasound at a Mechanical Index of 0.03 (at a frequency of 1.5 Mhz to 3.0 Mz) using a General Electric Vivid E9 Ultrasound system using a GE 4VD probe for 10 minutes via a transducer placed on the skin of the animal approximately 3-4 inches directly above the pancreas of the animal. The correct placing of the ultrasound transducer was effected by observing the appearance of opaqueness in the pancreas when the ultrasound was placed correctly to achieve stable cavitation of the ultrasound agent. At the end of insonation, porcine secretin was administered intravenously to the animal (0.2 to 0.4 mg/kg body weight). The pancreas of the animal subsequently produced pancreatic fluid which has collected to a volume of 50 mL (which took approximately 5 minutes) using the catheter positioned in the duodenum in the vicinity of the Ampulla of Vater/sphincter of Oddi. A pulsatile flow was observed.

Subsequent histological analysis of the sample obtained showed individual cells as well as large fragments of pancreatic epithelia tissue (see FIG. 1) had been induced to exfoliate into the pancreatic fluid by the ultrasound technique.

Example 2

A pig, denied food for 24 hours beforehand, was anesthetized for comfort and placed in a supine position on its side. Fluoroscopy was used to place a collecting catheter at an outlet of the pig's pancreas into the duodenum. Before the animal was insonated with ultrasound the area adjacent to the outlet of the pancreas (in the vicinity of the Ampulla of Vater/sphincter of Oddi) was cleaned using catheter suction. The animal was insonated with single frequency ultrasound at a Mechanical Index of 1.3 to 1.4 (e.g. at 2.0 Mz) for 10 minutes via a transducer placed on the skin of the animal approximately 3-4 inches directly above the pancreas of the animal. The correct placing of the ultrasound transducer was effected by observing the appearance of opaqueness in the pancreas when the ultrasound was placed correctly. At the end of insonation, secretin was administered intravenously to the animal (0.2 to 0.4 mg/kg body weight). The pancreas of the animal subsequently produced pancreatic fluid which has collected to a volume of 50 mL (which took approximately 5 minutes) using the catheter positioned in the duodenum in the vicinity of the Ampulla of Vater/sphincter of Oddi. A pulsatile flow was observed.

Subsequent histological analysis of the sample obtained showed individual cells of pancreatic epithelia tissue had been induced to exfoliate into the pancreatic fluid by the ultrasound technique. However, the animal was also observed to exhibit clear signs of pancreatitis, a sometime undesirable side-effect of pancreatic fluid collection. It was determined that a lower Mechanical Index of 1.3 to 1.4 was preferred to reduce possible pancreatitis.

Example 3

A pig, denied food for 24 hours beforehand, is anesthetized for comfort and placed in a supine position on its side. Fluoroscopy is used to place a collecting catheter at an outlet of the pig's pancreas into the duodenum. Before the animal is insonated with ultrasound the area adjacent to the outlet of the pancreas (in the vicinity of the Ampulla of Vater/sphincter of Oddi) is cleaned using catheter suction. The animal is insonated with multi-frequency (and optionally multi-phase, asymmetric wave) ultrasound at a Mechanical Index greater than 0.03 but not to exceed 1.3 (at frequencies of 1.5 Mhz to 3.0 Mz) for 10 minutes via a transducer which is placed on the skin of the animal approximately 3-4 inches directly above the pancreas of the animal. The correct placing of the ultrasound transducer is effected by observing the appearance of opaqueness in the pancreas when the ultrasound is placed correctly. At the end of insonation, secretin is administered intravenously to the animal (0.2 to 0.4 mg/kg body weight). Using a catheter positioned in the duodenum in the vicinity of the Ampulla of Vater/sphincter of Oddi, pancreatic fluid is collected to a volume of 50 mL and histological analysis performed on the sample.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES (1) Rahib L, Smith B D, Aizenberg R, et al. Projecting cancer incidence and deaths to 2030: the unexpected burden of thyroid, liver, and pancreas cancers in the United States. Cancer Res 2014; 74:2913-2921.

(2) Canto M I, Goggins M, Yeo C J, et al. Screening for pancreatic neoplasia in high-risk individuals: an EUS-based approach. Clin Gastroenterol Hepatol 2004; 2:606-621.

(3) Canto M I, Goggins M, Hruban R H, et al. Screening for early pancreatic neoplasia in high-risk individuals: a prospective controlled study. Clin Gastroenterol Hepatol 2006; 4:766-781.

(4) Canto M I, Hruban R H, Fishman E K, et al. Frequent detection of pancreatic lesions in asymptomatic high-risk individuals. Gastroenterol 2012; 142: 796-804;

(5) Yu J, Sadakari Y, Shindo K, et al. Digital next-generation sequencing identifies low-abundance mutations in pancreatic juice samples collected from the duodenum of patients with pancreatic cancer and intraductal papillary mucinous neoplasms. Gut 2017; 66:1677-1687.

(6) Endo Y, Morii T, Tamura H, et al. Cytodiagnosis of pancreatic malignant tumors by aspiration, under direct vision, using a duodenal fiberscope. Gastroenterol 1974; 67:944-51.

(7) Blackstone M O, Cockerham L, Kirsner J B et al. Intraductal aspiration for cytodiagnosis in pancreatic malignancy. Gastrointest Endosc 1977; 23:145-7.

(8) Nakaizumi A, Tatsuta M, Uehara H. et al. Cytologic examination of pure pancreatic juice in the diagnosis of pancreatic carcinoma. The endoscopic retrograde intraductal catheter aspiration cytologic technique. Cancer 1992; 70:2610-14.

10. The method of claim 1, wherein said microbubbles comprise sulfur hexafluoride lipid-type A microspheres.

11. The method of claim 1, wherein said insonating comprises applying said ultrasound at a frequency between 1.0 Mhz and 3.0 Mhz, said ultrasound comprising a single frequency, or multi-frequency and/or multi-phase ultrasound.

12. The method of claim 1, wherein said insonating comprises causing the exfoliation of fragments of epithelia including contiguous cells.

13. The method of claim 12, wherein said fragments include at least one sheet of epithelial cells.

14. The method of claim 12, wherein said fragments include at least one intact multi-cell tissue fragment.

15. The method of claim 1, wherein the insonation is applied so as to not elicit implosion of microbubbles within said pancreas.

---

---

What is claimed is:

1. A method of obtaining pancreatic cells from a subject comprising:
   administering an amount of a microbubble containing agent to the subject; and
   insonating a pancreas of the subject with an amount of ultrasonic energy effective to elicit stable cavitation and elicit exfoliation of cells into a duct of said pancreas by interaction of said energy with said microbubbles in said subject's pancreas, without creating inertial cavitation in said pancreas.

2. The method of claim 1, wherein insonating comprises insonating said pancreas with ultrasound at a mechanical index of less than 0.3.

3. The method of claim 2, wherein insonating comprises insonating said pancreas with ultrasound at a mechanical index of less than 0.03.

4. The method of claim 1, wherein the ultrasonic energy is emitted from a transducer array that includes a plurality of cavitation detectors for monitoring and localizing cavitation during the procedure.

5. The method of claim 1, wherein said insonating comprises insonating said pancreas for at least 5 minutes.

6. The method of claim 1, wherein said insonating comprises insonating using non focused ultrasound.

7. The method of claim 1, wherein said administering comprises administering intravenously.

8. The method of claim 1, wherein said administering comprises administering directly to said pancreas.

9. The method of claim 1, wherein said insonating comprises applying said ultrasound in at least two different positions on a coronal, sagittal or transverse plane of the pancreas.

16. The method of claim 1, wherein the insonation is with a pulse length of between 0.8 and 420 microseconds.

17. The method of claim 1, wherein the ultrasonic energy does not exceed a Mechanical Index of 1.3.

18. The method of claim 1 wherein said insonating comprises insonating a pancreas of the subject with an amount of ultrasonic energy from a multi-frequency array effective to achieve an asymmetric ultrasound wave at a predetermined point in the pancreas.

19. The method of claim 1, further comprising positioning a catheter or other collecting device at an opening of a pancreatic duct in the subject.

20. The method of claim 19, further comprising obtaining a sample of pancreatic secretion using the catheter or other collecting device.

21. The method of claim 20, further comprising analyzing the sample of the pancreatic secretion obtained so as to determine if the sample contains pancreatic cancer cells or pancreatic dysplasia cells, or is non-pathological.

22. A method of treating a subject for a pancreatic disorder comprising:
   a) determining if the subject has pancreatic dysplastic cells or pancreatic cancer cells in their pancreas by the method of claim 21, and
   b) effecting chemotherapy, radiotherapy, immunotherapy or a pancreatectomy in a subject found in a) to have pancreatic dysplastic cells or pancreatic cancer cells in their pancreas.

23. The method of claim 22, wherein determining if the subject has pancreatic dysplastic cells or pancreatic cancer cells in their pancreas is effected through one or more of cellular morphological analysis, tissue morphological analysis, or biomolecular marker analysis.

24. The method of claim 20, wherein said ultrasound energy is sufficient so that an amount of epithelial cells exfoliated into said sample is at least double an amount which would be exfoliated without said insonation.

25. The method of claim 1, wherein said insonating comprises insonating the pancreas of the subject with an amount of ultrasonic energy effective to elicit exfoliation of cells into a duct of said pancreas by mechanical interaction of said microbubbles with said subject's pancreas, without creating inertial cavitation in said pancreas.

26. The method of claim 1, wherein said microbubble containing agent is an ultrasound contrast agent.

27. A method of obtaining pancreatic cells from a subject comprising:

administering an amount of a contrast bubble agent to the subject; and insonating a pancreas of the subject with an amount of ultrasonic energy effective to elicit exfoliation of cells into a duct of said pancreas by mechanical interaction of said contrast bubble agent with said subject's pancreas, without creating inertial cavitation in said pancreas.

* * * * *